United States Patent [19]
Eberle

[11] B 3,997,670
[45] Dec. 14, 1976

[54] 1-DIOXOLANYLPROPYL-3-INDOLEACRYLIC ACID ESTERS
[75] Inventor: Marcel K. Eberle, Madison, N.J.
[73] Assignee: Sandoz, Inc., E. Hanover, N.J.
[22] Filed: Feb. 6, 1975
[21] Appl. No.: 547,547
[44] Published under the second Trial Voluntary Protest Program on February 24, 1976 as document No. B 547,547.
[52] U.S. Cl. .................. 424/274; 260/326.13 R; 260/326.16
[51] Int. Cl.² ........................ C07D 209/18
[58] Field of Search ...... 260/326.13 HO, 326.13 B; 424/274

Primary Examiner—Lewis Gotts
Assistant Examiner—S. P. Williams
Attorney, Agent, or Firm—Gerald D. Sharkin; Robert S. Honor

[57] ABSTRACT 1-dioxolanylpropyl-3-indoleacrylic acid esters, e.g., 1-[3-(2-methyl-2-dioxolanyl)propyl]-3-indoleacrylic acid ethyl ester, are prepared by reacting a corresponding 1-dioxolanylpropyl-3-indolecarboxaldehyde with carbalkoxymethylene triphenylphosphorane and are useful as hypolipidemic agents.

6 Claims, No Drawings

1-DIOXOLANYLPROPYL-3-INDOLEACRYLIC ACID ESTERS

This invention relates to 1-dioxolanylpropyl-3-indoleacrylic acid esters, which exhibit hypolipidemic activity. In particular, it relates to 1-[3-(2-substituted or unsubstituted-2-dioxolanyl)propyl]-3-indoleacrylic acid esters, intermediates thereof and to processes for their preparation.

The compounds of this invention may be represented by the following structural formula:

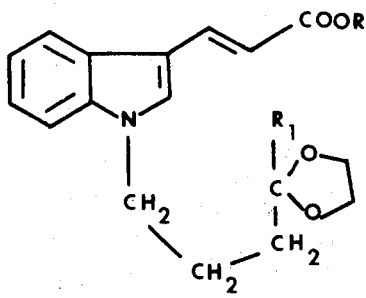

where
R represents straight chain lower alkyl, i.e., straight chain alkyl having 1 to 4 carbon atoms, e.g., methyl, ethyl, propyl and the like, and
$R_1$ represents hydrogen, straight chain lower alkyl as defined above, or unsubstituted phenyl.

The compounds of formula (I) are prepared according to the following reaction scheme:

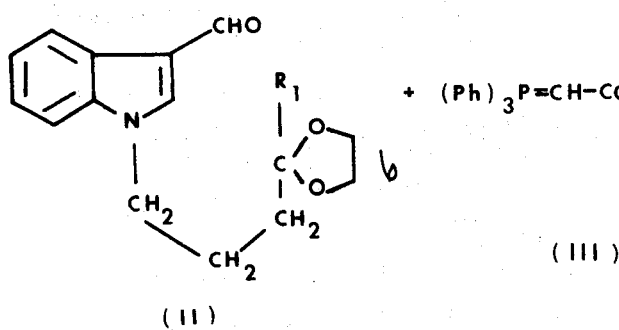 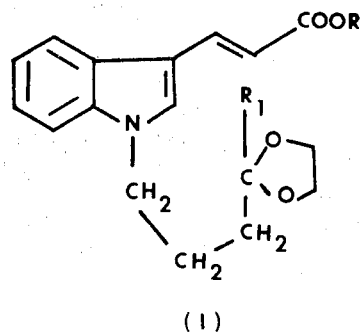

where R and $R_1$ are as defined above.

The compounds of formula (I) are prepared by treating a compound of the formula (II) with a compound of the formula (III) in the presence of an inert organic solvent. Although the particular solvent used is not critical, it is preferred that the reaction be carried out in the presence of ether, such as diethylether, tetrahydrofuran and the like, the lower alkanols, e.g., methanol, ethanol and the like, or the aromatic hydrocarbons such as benzene, toluene and the like, preferably toluene. The temperature of the reaction is not critical, but it is preferred that the reaction be carried out at a temperature between about 50° to 150°C., preferably the reflux temperature of the solvent. The reaction may be run from about 6 to 36 hours, preferably from about 10 to 15 hours. The product is recovered using conventional techniques, e.g., column chromatography.

The compounds of formula (II) are prepared by the following reaction scheme:

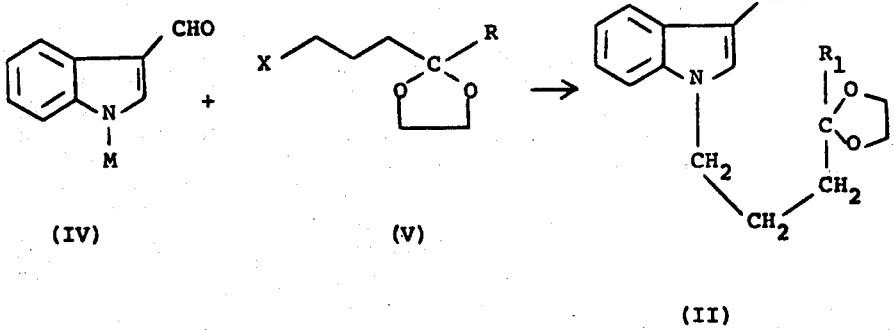

where
M represents an alkali metal, i.e., sodium, potassium, or lithium,
X represents fluoro, chloro or bromo, and
R and $R_1$ are as defined above.

The compounds of formula (II) are prepared by treating a compound of the formula (IV) with a compound of the formula (V) in the presence of an inert organic solvent. Although the particular solvent used is not critical, it is preferred that the reaction be carried out in the presence of ether, such as diethyl ether, tetrahydrofuran and the like, the lower alkanols, such as methanol, ethanol and the like, dimethylacetamide, or dimethylformamide, the latter being especially preferred. The temperature of the reaction is not critical, but it is preferred that the reaction be carried out at a temperature between about 0° to 150°C., preferably between about 30° to 70°C. The reaction may be run from 8 to 30 hours, preferably from about 10 to 15 hours. The product is recovered using conventional techniques, e.g., crystallization.

Many of the compounds of formulae (III), (IV), and (V) are known and may be prepared by methods described in the literature. The compounds of formulae (III), (IV), and (V) not specifically disclosed may be prepared by analogous methods from known starting materials.

The compounds of formula (I) are useful because they posses pharmacological activity in animals as hypolipidemic agents, particularly as hypolipoproteinemic agents as indicated by the fall in cholesterol and triglyceride levels in male albino Wistar rats weighing 110 to 130 g. initially. The rats are maintained on drug-free laboratory chow diet for seven days and then divided into groups of 8 to 10 animals. Each group with the exception of the control is then given orally 30 to 250 milligrams per kilogram of body weight per diem of the compound for six days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, E., and Lederer, H., 1965, Technicon Symposium, Mediad, Inc., N.Y., 345–347) are added; and the mixture is shaken for one hour. Cholesterol and triglyceride levels are determined simultaneously on the same sample by Technicon N 24 A (cholesterol) and N 78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspensions, dispersions, emulsions and the like, e.g., a sterile injectable aqueous solution. The dosage will vary depending upon the mode of administration utilized and the particular compound employed.

The hypolipidemic effective dosage of compounds (I) employed in the alleviation of lipidemia may vary depending on the particular compound employed and the severity of the condition being treated. However, in general, satisfactory results are obtained when the compounds of formula (I) are administered at a daily dosage of from about 4.0 milligrams to about 250 milligrams per kilogram of animal body weight, preferably given in divided doses two to four times a day, or in sustained release form. For most large mammals, the total daily dosage is from about 300 milligrams to about 2000 milligrams. Dosage forms suitable for internal use comprise from about 75 to about 1000 milligrams of the active compound in intimate admixture with a solid or liquid pharmaceutically acceptable carrier or diluent.

A representative formulation suitable for oral administration two to four times a day for the treatment of lipidemia is a capsule prepared by standard encapsulating techniques which contains the following:

| Ingredients | Weight (mg.) |
| --- | --- |
| 1-[3-(2-methyl-2-dioxolanyl)propyl]-3-indoleacrylic acid ethyl ester | 150 |
| inert solid diluent (starch, lactose, kaolin) | 300 |

EXAMPLE 1

1-[3-(2-methyl-2-dioxolanyl)propyl]-3-indolecarboxaldehyde.

A suspension of 10.6 g. (0.44 mole) of sodium hydride in 50 ml. of dry dimethylformamide is treated dropwise with a solution of 58 g. (0.40 mole) of indole-3-carboxaldehyde in 200 ml. of dimethylformamide. An exothermic reaction is observed with the temperature rising to 70°C. The resulting mixture is stirred for one hour. To the resulting mixture there is added 69 g. (0.42 mole) of 2-methyl-2(3-chloropropyl)-dioxolane, and the mixture is maintained overnight at room temperature. The solvent is evaporated and the residue is extracted with ether, washed with water and dried over anhydrous magnesium sulfate. Following the evaporation of the solvent, the residue is crystallized from ether/hexane to give 1-[3-(2-methyl-2-dioxolanyl)-propyl]-3-indolecarboxaldehyde, m.p. 52°–55°C.

Following the above procedure and using in place of 2-methyl-2(3-chloropropyl)-dioxolane, an equivalent amount of a) 2-phenyl-2(3-chloropropyl)-dioxolane, or
b) 2-(3-chloropropyl)-dioxolane, there is obtained a) 1-[3-(2-phenyl-2-dioxolanyl)propyl]-3-indolecarboxaldehyde, or
b) 1-[3-(2-dioxolanyl)propyl]-3-indolecarboxaldehyde, respectively.

EXAMPLE 2

1-[3-(2-methyl-2-dioxolanyl)propyl]-3-indoleacrylic acid ethyl ester.

A mixture of 27.3 g of 1-[3-(2-methyl-2-dioxolanyl)-propyl]-3-indolecarboxaldehyde (0.1 mole) and 40 g. (0.11 mole) of carbethoxymethylene triphenylphosphorane in 400 ml. of toluene is heated at reflux overnight. The resulting cold solution is filtered through a Silica gel column to remove the inorganic material to give 1-[3-(2-methyl-2-dioxolanyl)propyl]-3-indoleacrylic acid ethyl ester, m.p. 61°–62°C.

Following the above procedure and using in place of 1-[3-(2-methyl-2-dioxolanyl)propyl]-3-indolecarboxaldehyde, an equivalent amount of a) 1-[3-(2-phenyl-2-dioxolanyl)propyl]-3-indolecarboxaldehyde, or
b) 1-[3-(2-dioxolanyl)propyl]-3-indolecarboxaldehyde, there is obtained a) 1-[3-(2-phenyl-2-dioxolanyl)propyl]-3-indoleacrylic acid ethyl ester, or
b) 1-[3-(2-dioxolanyl)propyl]-3-indoleacrylic acid ethyl ester, respectively.

Also following the above procedure and using in place of carbethoxymethylene triphenylphosphorane, an equivalent amount of carbmethoxymethylene triphenylphosphorane, there is obtained c) 1-[3-(2-methyl-2-dioxolanyl)propyl]-3-indoleacrylic acid methyl ester, m.p. 76°–78°C.

The 1-[3-(2-methyl-2-dioxolanyl)propyl]-3-indoleacrylic acid ethyl ester is an effective hypolipidemic agent when orally administered to an animal suffering from lipidemia at a dosage of 150 mg. four times per day.

What is claimed is:

1. A compound of the formula

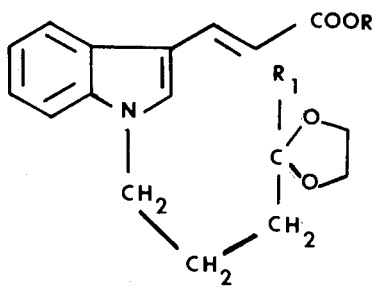

where
R represents straight chain lower alkyl having 1 to 4 carbon atoms, and
$R_1$ represents hydrogen, straight chain lower alkyl having 1 to 4 carbon atoms, or unsubstituted phenyl.

2. A compound of the formula

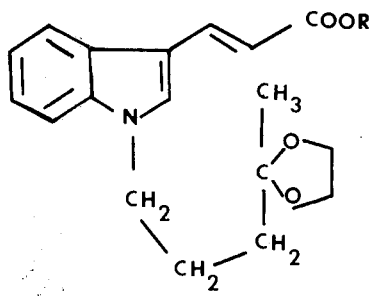

where R is as defined in claim 1.

3. The compound of claim 2 which is 1-[3-(2-methyl-2-dioxolanyl)propyl]-3-indoleacrylic acid ethyl ester.

4. The compound of claim 2 which is 1-[3-(2-methyl-2-dioxolanyl)propyl]-3-indoleacrylic acid methyl ester.

5. A pharmaceutical composition comprising a compound of claim 1 and a pharmaceutically acceptable diluent or carrier therefor.

6. A method of treating lipidemia which comprises administering to a mammal in need of said treatment a hypolipidemic effective amount of a compound of claim 1.

* * * * *